United States Patent [19]

Riedweg et al.

[11] Patent Number: 5,009,638
[45] Date of Patent: Apr. 23, 1991

[54] BREAST PUMP

[75] Inventors: Robert Riedweg, Eich; Klaus Schlensog, Hünenberg, both of Switzerland

[73] Assignee: Ameda AG, Switzerland

[21] Appl. No.: 486,418

[22] Filed: Feb. 28, 1990

[30] Foreign Application Priority Data

Mar. 1, 1989 [CH] Switzerland ............... 751/89

[51] Int. Cl.$^5$ .............................................. A61M 1/06
[52] U.S. Cl. ....................................... 604/74; 604/346
[58] Field of Search ................................. 604/74–76, 604/346; 119/14.47–14.53

[56] References Cited

U.S. PATENT DOCUMENTS

| 3,822,703 | 7/1974 | Davisson | 128/281 |
| 4,573,969 | 3/1986 | Schlensog et al. | 604/74 |
| 4,673,388 | 6/1987 | Schlensog et al. | 604/74 |
| 4,799,922 | 1/1989 | Beer et al. | 604/74 |

FOREIGN PATENT DOCUMENTS 2166353A 9/1984 United Kingdom .

*Primary Examiner*—Stephen C. Pellegrino
*Assistant Examiner*—Michael Rafa
*Attorney, Agent, or Firm*—Wigman & Cohen

[57] ABSTRACT

The breast pump comprises a milk reservoir and a flanged closure member for connection with the reservoir; the closure member comprises a suction bell and a suction pump suitable for single-handed manual operation and includes (a) a cylinder integrally connected with the closure member; (b) a piston for reciprocating motion within the cylinder between a first or lower position and a second or upper position, and (c) a spring-loaded actuator for insteraction with the piston.

10 Claims, 2 Drawing Sheets

BREAST PUMP

BACKGROUND OF THE INVENTION

(1) Field of the Invention

The invention generally relates to breast pumps and specifically to manually operable breast pumps of the type having a suction pump and being suitable for actuation with one hand only.

(2) Description of the Prior Art

Breast pumps for manual operation of the type disclosed, for example, in Applicants' U.S. Pat. No. 4,573,969 (EP 116,186) will normally be held in one hand, generally around the suction bell and near the breast while the other hand actuates motion of that pump component that causes suction.

Various improvements of such pumps have been introduced since, e.g. use of a small battery-operated motor as disclosed in Applicants' U.S. Pat. No. 4,673,388, or soft inserts into the suction bell as disclosed in U.S. Pat. No. 4,799,922.

Many prior art manual breast pumps of the general type disclosed in U.S. Pat. No. 3,822,703 can be operated "single-handed" in the sense that the breast pump is held and operated with one hand only and this may be advantageous because the mother will then be able to stimulate or press the breast so as to improve lactation and completeness of the milk discharge. Single-handed breast pumps have suffered from one or more disadvantages including poor visual control of operation (including actual milk discharge and lactation of the breast) and maintenance (i.e. cleaning or control of cleaning effectiveness). For example, a single-handed breast pump suggested more recently (e.g. in published British Pat. Application No. 2,166,353-A), while avoiding some disadvantages of previous single-handed breast pumps by replacing the conventional rubber ball with a pump arrangement, fails to provide a satisfactory solution. This prior art pump comprises a milk reservoir and a closure member for connection therewith; the closure member comprises a suction bell and a suction pump which, in turn, includes a cylinder integrally connected with the closure member, a piston for reciprocating motion within the cylinder and an actuator formed of a handle and a steel spring that is loaded (i.e. accumulates energy) when the handle is pressed downwards causing suction by lifting the piston within the cylinder; upon release of the handle the steel spring causes the handle to revert into its rest position and brings the piston back into its lowermost position within the cylinder. However, the use of metal components is not favored for breast pumps and the structure of the prior art actuator precludes sufficient visual control. Further, pumping by means of the handle involves an essentially asymmetrical motion which may cause the suction bell to be displaced more than is felt by the mother to be comfortable because of undesired axial nipple displacement or other irritation.

OBJECTS OF THE INVENTION

Accordingly, it is a primary object of the invention to provide for a novel manually operable breast pump of the single-handed type which provides for an improved and more symmetric actuation of the suction pump, requires no metallic components, and provides for better visual control of milk discharge from the nipple.

Further objects will become apparent as the specification proceeds.

SUMMARY OF THE INVENTION

Now, in order to implement these objects the invention provides for a breast pump of the type defined above, i.e. comprising a milk reservoir and a flanged closure member for connection therewith; said closure member comprising a suction bell and a suction pump suitable for single-handed manual operation and including: (a) a cylinder integrally connected with said closure member, (b) a piston means for reciprocating motion within said cylinder between a first or lower position and a second or upper position, and (c) a spring-loaded actuator for interaction with said piston means According to the present invention the actuator is formed by a yoke means or structure comprising an elongated spring member having a first or normal position and being reversibly deformable into a second or elastically bent position; when in this position, a front view of the yoke means will generally show a "mushroomtype" shape formed by the upper arc of the bent spring and with sides formed by a pair of lateral legs as explained in more detail below; the elongated spring member has two ends (in longitudinal direction) and is connected with the piston means near the longitudinal center of the spring member; the yoke structure further comprises a pair of elongated lateral legs each having a lower end and an upper end; each of the lower leg ends is connected with an anchoring member provided directly or via a preferred intermediate member on said closure member; each of the upper ends of the elongated lateral legs is connected with the spring member at one of the longitudinal ends thereof, and the yoke means or structure is generally dimensioned for single-handed manual compression (i.e. pressing together) of the lateral legs and for elastically deforming the spring member thereby so that the piston means is displaced upwards within the cylinder and permits the spring member to revert into its first or normal position when the lateral legs are released; consequently, the piston means will return into its first or lower position and a subsequent pumping cycle by pressing together (i.e. towards the axis of the cylinder) the lateral legs can be started.

DISCUSSION OF PREFERRED EMBODIMENTS

For many embodiments of the invention it will be preferred that the yoke structure has a generally symmetrical configuration and that the main constituents thereof, i.e. the lateral legs and the elongated spring, will be interconnected with each other and with their operationally adjacent constituents of the pump in a generally movable and preferably pivotable or hinged manner; it is even more preferred if the connection of the yoke structure with the closure member, on the one hand, and the piston, on the other hand, is effected by "snap-on" hinges, e.g. where the male part of the hinges and the female parts thereof may be disconnected and reconnected because of some elastic deformation of the hinge members.

It is generally preferred that the lateral legs as well as the elongated spring member are made of a synthetic plastic material capable of being sterilized by heat. Typical examples include such materials as polyacetals, polycarbonate and polypropylene. The legs should have a significantly higher bending resistance than said spring member.

According to another preferred embodiment the anchoring member is an open-ended (e.g. a circular or annular structure preferably made of a plastic material of the type mentioned, with a segment of the circle or annulus cut away) ring for snap-on connection with a substantially peripheral guide recess extending around a major portion of the outer surface of the closure member or "groove" provided on the flanged closure member to permit limited rotational displacement of the yoke structure around an axis of rotation commonly defined by the cylinder of the pump and the peripheral recess. This permits that the mother using the pump may select exactly that position of the yoke structure which will be most comfortable to her as determined inter alia by the size and strength of her hand and the preferred position she would take when feeding her baby.

Preferably, the open ring member is provided with arresting means, e.g. indentations of the open-ended ring cooperating with a protrusion of the guide recess or groove in the closure member for temporarily maintaining the yoke structure in an operational position of displacement as selected by the mother.

Generally, the closure member will have a circular flange provided with a thread or bayonet-type connection for engagement with a corresponding thread or bayonet-type connector provided at the opening of the milk reservoir; the circular flange (generally with the attached reservoir) defines a first axis of rotation; the cylinder of the pump and the said circular groove commonly define a second axis of rotation, said first and said second axis of rotation being offset relative to each other by an angle of between about 10° and about 20°, and wherein the suction bell defines a third axis of rotation arranged at an angle of about 90° relative to the second axis of rotation. This particular arrangement has been found to provide optimum visual control of the nipple area and milk discharge combined with a most comfortable general shape and structure of the breast pump when used by a mother in any body position which would be preferred when holding and breast-feeding a baby.

As will be apparent from the drawings, the term "suction bell" as used herein is intended to generally refer to prior art structures, preferably to the structure disclosed and defined in some detail in the above mentioned U.S. Pat. No. 4,573,969 to Applicants which bells are believed to have become an industrial standard in the art of breast pumps. Accordingly, the disclosure of U.S. Pat. No. 4,573,969 with regard to suction bells as well as the shapes and dimensions thereof, inserts or adapters for breasts of different sizes, as well as suitable polymers for producing the suction bell or other components of the closure member is incorporated herein by way of reference.

As briefly mentioned above, it is preferred that the piston of the suction pump is connected with the spring member in a manner that provides for ease of assembly and disassembly and/or can serve to limit maximum suction, i.e. will disconnect when the suction generated by means of the suction pump within the suction bell (closed at the normally open front by the mother's breast) exceeds a predetermined maximum, e.g. a pressure differential between the ambient pressure and that within the suction bell of about $-400$ millibars (i.e. the absolute pressure within the suction bell upon maximum suction will be 1000-400 millibars). Generally, such differential will be in the range of from about 1 to about 300 mb.

Generally, it is preferred that substantially all components of the closure member are made of a transparent or translucent material to facilitate control of operation and maintenance of said pump. This is less critical, of course, for seal rings, connectors and even the spring and the lateral legs but is believed to be rather crucial for the pump, the suction bell and the interconnecting portions of the closure member.

According to a further embodiment of the invention the breast pump is additionally provided with a "bellows", i.e. an essentially cylindrical hollow and flexible structure made of a heat-resistant elastomer, such as silicone rubber, that will fit into the bore of the cylinder when the piston has been removed. The bellows is connected with a flexible tube for connection with an external source of an oscillating negative pressure such as normally produced by hospital-sized electrical breast pumps which can be rented in many towns. In other words, the flanged closure means of a breast pump according to the invention can be easily transformed into a "personalized" component of a rented pump because any contamination of the milk from the rented pump can be safely precluded by the bellows. When in this mode the breast pump is not manually operated but still provides improved visual control and comfortable body position.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various Figures there have been generally used the same reference characters, or end digits, to denote the same or analoguous components and wherein.

DETAILED DESCRIPTION OF THE DRAWINGS

Describing now the drawings, it is to be understood that the illustration is given by way of example and not limitation and that only enough of the construction of the breast pump has been shown as needed for those skilled in the art to readily understand the underlying principles and concepts of the present invention while simplifying the showing of the drawings.

Figure 1A:
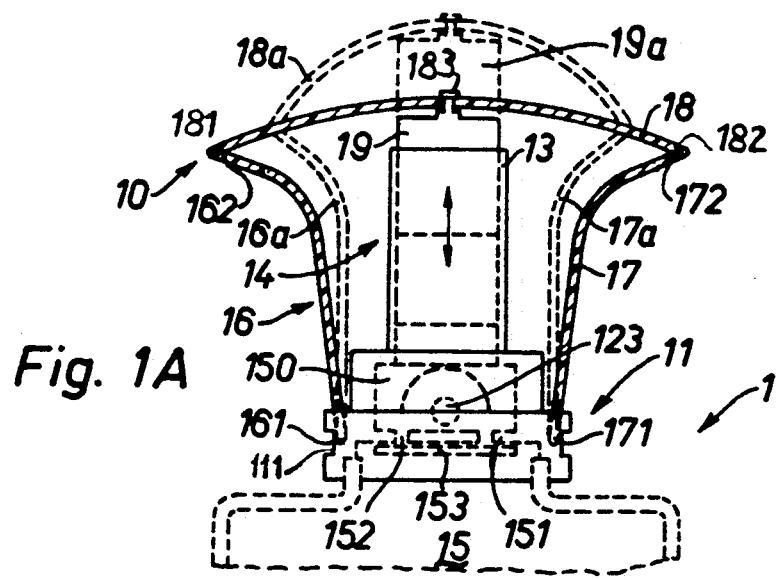
FIG. 1A is a diagrammatical presentation of a first embodiment of the present breast pump when viewed from the side opposite the suction bell and with the yoke structure both at rest as in extended position (shown in broken lines) to show the preferred symmetrical structure of the actuator according to the invention.
Figure 1B:
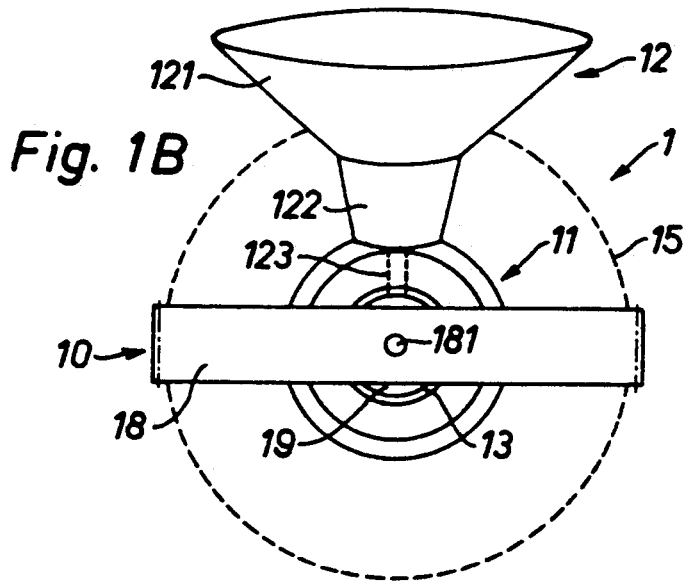
FIG. 1B is a top view of the embodiment shown in FIG. 1A.

Turning attention now to FIGS. 1A and 1B of the drawing, a first embodiment of the symmetrically designed yoke structure of a single-handed breast pump 1 according to the invention is shown in a schematic presentation as viewed from the side of the breast pump 1 that is opposed to the suction bell, the latter not being indicated in FIG. 1A but for clarity.

Closure member 11 typically made of a transparent and thermostable (i.e. capable of being sterilized by hot air or water at temperatures of up to 120° C.) polymer such as a polycarbonate, is releasably connected in a manner known per se with a suitable milk reservoir 15 as disclosed in the art cited above and shown in part only and in broken lines. Suction bell 12 is shown diagrammatically in the top view of FIG. 1B and includes, in a manner known per se, a flanged outer portion 121 and a frustro-conical transition 122 to receive the nipple of the mother's breast and to permit passage of the milk into and through closure member 11. Suction bell 12 as well as cylinder 13 of the suction pump 14 will generally be made as an integral, i.e. monolithical structure of the type produced by injection molding or other conventional polymer molding methods. In line with this consideration, closure member 11, suction bell 12 and cylinder 13 will in general be made of the same polymer material.

A bore or other conduit 123 is provided in closure member 11 for passage of milk from suction bell 12 into a chamber 150 having a lower bottom 151 provided with one or more apertures 152 and a valve means 163 that permits passage of milk into reservoir 15 but limits the volume within which a reduced pressure must be produced intermittently. Such valves and many modifications thereof, again, are conventional in breast pumps and will not be further discussed herein.

Suction pump 14 consists essentially of the cylinder 13 just mentioned and a piston 19, generally with an annular seal (not shown in FIGS. 1A, 1B). Piston 19 is arranged for reciprocating motion (indicated by a double arrow in fig 1A) between an upper and a lower position The upper end of piston 19 is connected, preferably in a releasable manner, such as by a snap-on hinge, with an elongated and generally flat spring member 18 having two ends 181, 182. A connection, hinge 30 or joint 183 between spring 18 and piston 19 is provided substantially at the (longitudinal) center of spring 18 while spring ends 181, 182 are hingedly (i.e. by a hinge or similar pivotable joint) connected with the two elongated lateral legs 16, 17. These lateral legs, in turn, are releasably connected at their lower ends 161, 171, again preferably in a hinged manner (not shown) with an anchoring member, e.g. a recess 111, of closure 11.

The characteristic design (also termed "symmetric" herein) of the actuator 10 (formed essentially by the two lateral legs 16, 17 and the elongated spring 18) will be apparent when considering actuation of pump 14 by displacement of piston 19 in the directions of the double arrow: upon compression between the thumb and the fingers of a user's hand legs 16, 17 will be pressed towards each other (and the longitudinal axis of piston 13) into a position shown in broken lines and designated as 16a, 17a. Consequently, spring 18 will be bent elastically and be displaced into the position indicated as 18a and piston 19 will be moved into its uppermost position 19a.

As a result, suction will be generated by pump 14 and if suction bell 12 is closed by a mother's breast, such suction will cause a discharge of milk into reservoir 15.

When the compression of lateral legs 16, 17 is terminated by release thereof or by reduced finger pressure, spring 18 will tend to return from its bent position 18a into its normal or rest position shown in FIG. 1A. As will be apparent from this discussion, the entire operating cycle between a first compression of legs 16, 17 and a subsequent compression after intermediate release, is essentially "symmetric" from a kinetic point of view of the operation of actuator 10, i.e. relative to any motion that would cause displacement of suction bell 12 relative to the breast. When comparing such symmetric actuation according to the invention, the advantages over prior art single-handed pumps of the type having a laterally protruding lever will become apparent.

From the operation of actuator 10 just explained, it will be apparent that the main area of bending deformation should be restricted to spring 18. In other words, the "bending resistance" of legs 16, 17 should be significantly higher than the bending resistance of spring 18. Such bending resistance of legs 16, 17 can be achieved by means of shape, dimension and materials in a manner known per se. A preferred shape of legs 16, 17 is illustrated in FIG. 1A with inwardly bent upper portions of the lateral legs but this is not believed to be generally critical. The "mushroom"-type shape of actuator 10, both at rest and in compressed state, is, however, preferred because of ergonomic considerations.

Figure 2:
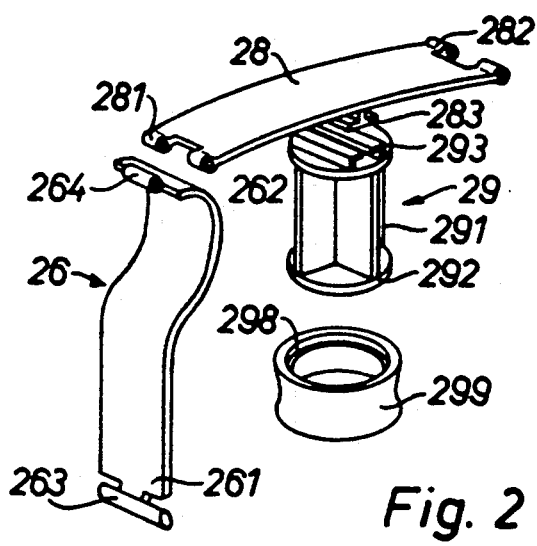
FIG. 2 is an exploded view of components of the yoke structure where one of the lateral legs has been omitted for simplicity.

FIG. 2 illustrates, in a semi-diagrammatic exploded and perspective view, an embodiment of the interconnection between the actuator and the pump according to the invention. Only one lateral leg 26 is shown in FIG. 2 for simplicity (the other leg being shaped in the same manner). The lower end 261 of leg 26 is provided with the "male" portion 263 of a hinge of which the other part, e.g. a recess in an anchoring portion of the closure member, is not shown. It should be noted, however, that the term "anchoring member" as used herein is intended to include both a simple recess or similar fixing member in the closure member as well as a separate constituent that is moveably connected with the lower ends of the lateral legs and is, in turn, moveably connected with the closure member as will be illustrated hereinbelow. First, however, FIG. 2 illustrates a hinged connection between the upper end 264 of leg 26 and one end 281 of spring 28. Both ends 264 and 281 can be interconnected by means of a splint, bolt, rod or the like means (not shown) which may be separate or integral components of the resulting hinges. A protruding and profiled portion 283 is provided near the longitudinal center of spring 28 between its ends 281, 282 to interfit with a correspondingly shaped portion 293 at the upper end of piston 29. A "T"-shaped profile is shown merely for illustration and any other types of interfitting connectors may be used. Piston 29 might be a closed, i.e. cylindrical or tubular, structure or be formed as a cross-type profile 291 with a circular lower disc end 292 suitable to receive and hold a conventional sealing ring 299, e.g. having an internal groove 298 for snap-on connection with disc end 292.

Figure 3:
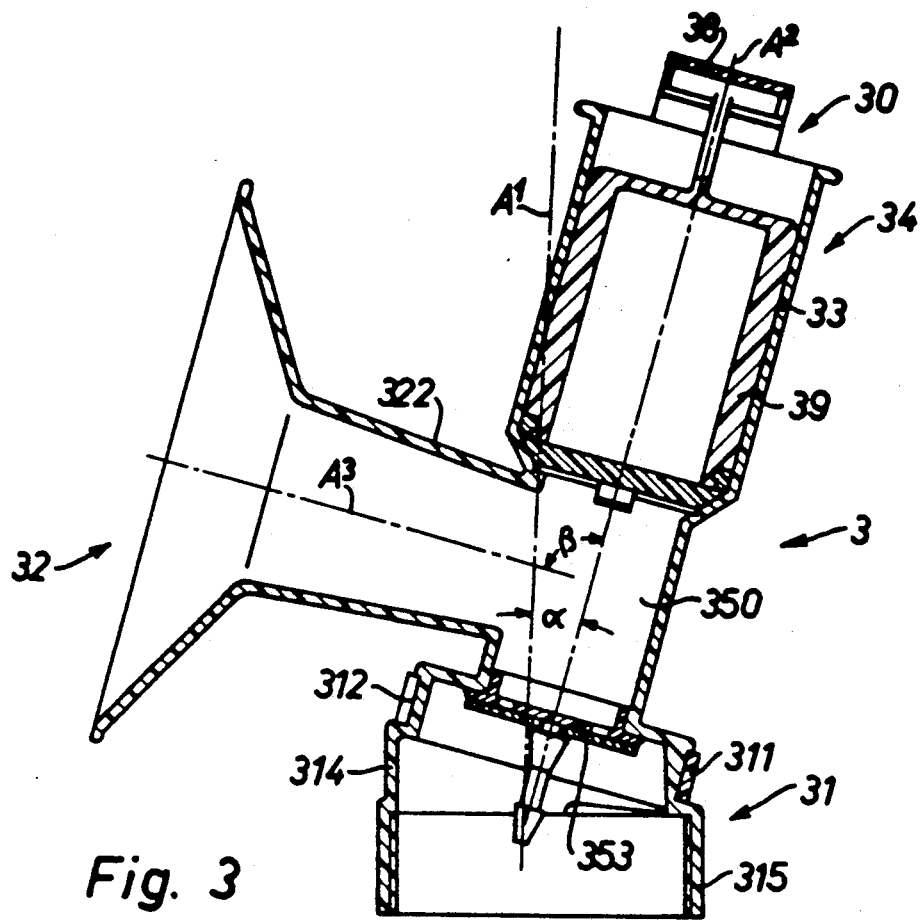
FIG. 3 is a semi-diagrammatical sectional side view of a second embodiment of the breast pump according to the invention with the lateral leg members omitted for clarity.

FIG. 3 shows a sectional view of a preferred embodiment of pump 3 in which the suction bell 32, pump 34 and spring 38 are substantially as explained in connection with FIGS. 1A and 1B (lateral legs not illustrated for clarity) but where a preferred general shape of the pump as well as a preferred type of anchoring member of the actuator 30 are shown. To this end, closure member 31 is provided with a flanged end 315 for connection with a milk reservoir (not shown) and an angular tube segment 314 which, in turn, offsets axis $A^1$ (an axis of rotation defined by flange 315 and the milk reservoir) relative to the rotational axis $A^2$ of pump 34 or its cylinder 33, respectively, by an angle $\alpha$ of between about 10° and about 20°. Because the rotational axis $A^3$ of suction bell 32 is at an angle $\beta$ of about 90° relative to axis $A^2$, the nipple-surrounding portion 322 of suction bell 32 will be perfectly visible to the mother so that she can watch and control the milk discharge. It is believed that such visual contact is most favorable for the lactation process.

Figure 4:
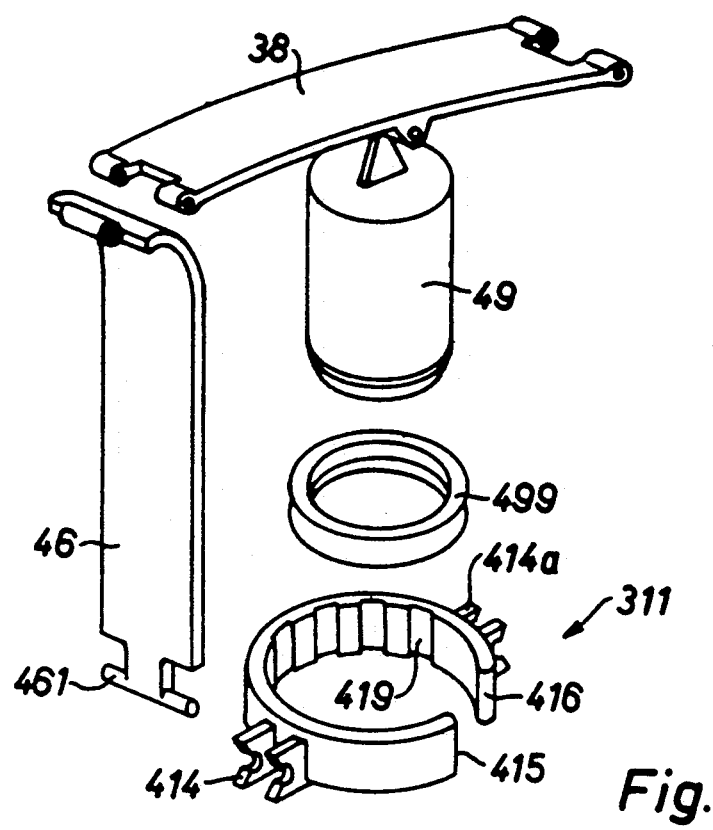
FIG. 4 is an exploded view of components of the yoke structure where the lateral legs (one omitted for simplicity) are hingedly connected at their lower ends with a slidable open ended ring.

FIG. 3 further illustrates a preferred anchoring means for the lateral legs by means of an open-ended ring 311 that is slidingly mounted in a peripheral recess 312 of closure 32 as explained more fully in FIG. 4. It will be noted that the illustration of FIG. 3 further shows preferred structures for the members 33, 39 of pump 34, the arrangement of chamber 350 and the valve means 35, and a preferred connection between piston 39 and spring 38.

FIG. 4 corresponds, in essence, with FIG. 2 except that the lower ends of the lateral legs (only end 461 of leg 46 shown) will be inserted into snap-on brackets as represented diagrammatically by 414. A pair of such brackets or other connectors 414, 414a is integrally connected with ring 311 explained above having two ends 415, 416. Such ring will preferably be made of a flexible polymer composition of the type explained above and can be snapped on or snapped off the peripheral recess 312 shown in FIG. 3. Arrestor means, e.g. grooves 419, can be provided at the inside of ring 311 to cooperate with one or more corresponding protrusions of peripheral recess 312. As a result, a desired position of the actuator as indicated partially in FIG. 4 relative to the axis $A^2$ will be held after it has been selected by the user for optimum comfort. It will be apparent that the actuator could be removed from closure member 31 together with the ring 311 as soon as the snap-on connection between spring 38 and piston 39 is released.

The advantages of the present invention, as well as certain changes and modifications of the disclosed embodiments thereof, will be readily apparent to those skilled in the art. It is Applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that prior art allows.

What is claimed is:

1. A breast pump comprising a milk reservoir and a closure member for connection with said reservoir; said closure member comprising a suction bell and a suction pump suitable for single-handed manual operation and including: (a) a cylinder integrally connected with said closure member; (b) a piston means for reciprocating motion within said cylinder between a first or lower position and a second or upper position, and (c) a spring-loaded actuator for interaction with said piston means; wherein said actuator is formed by a yoke means comprising an elongated spring member having a first or normal position and being reversibly deformable into a second or elastically bent position, said spring member having two ends and being connected with said piston means substantially intermediate between said two ends, and said yoke further comprising a pair of elongated lateral legs each having a lower end and an upper end, each of said lower ends being connected with an anchoring member on said closure member, each of said upper ends of said elongated lateral legs being connected with said spring member near one of said two ends thereof, said yoke means being dimensioned for single-handed manual compression of said lateral legs and for elastically deforming said spring member by said compression so as to upwardly displace said piston means within said cylinder upon said manual compression and permitting said spring member to revert into its first or normal position when said lateral legs are released from said manual compression for returning said piston means into said first or lower position.

2. The breast pump of claim 1 wherein said yoke means has an essentially symmetrical structure and wherein said lower ends of said lateral legs are hingedly connected with said anchoring member while said upper ends of said lateral legs are hingedly connected with said ends of said spring member.

3. The breast pump of claim 2 wherein said lateral legs as well as said elongated spring members are made of a synthetic plastic material capable of being sterilized by heat and wherein said legs have a higher bending resistance than said spring member.

4. The breast pump of claim 1 wherein said anchoring member is an open ring member for snap-on connection with an essentially peripheral guide recess provided on said closure member to permit limited rotational displacement of said yoke around an axis ($A^2$) of rotation commonly defined by said cylinder and said peripheral guide recess.

5. The breast pump of claim 4 wherein said open ring member is provided with arresting means for temporarily maintaining said yoke means in an operational position of said displacement.

6. The breast pump of claim 1 wherein said closure member has a circular flange for engagement with said reservoir to commonly define a first axis ($A^1$) of rotation, and wherein said cylinder of said pump and said circular groove commonly define a second axis ($A^2$) of rotation, said first and said second axis of rotation being offset relative to each other by an angle ($\alpha$) of between about 10° and about 20°, and wherein said suction bell defines a third axis ($A^3$) of rotation arranged at an angle ($\beta$) of about 90° relative to said second axis of rotation.

7. The breast pump of claim 1 wherein said piston means is hingedly connected with said elongated spring member.

8. The breast pump of claims 2 or 6 wherein said hinged connections are snap-on connections for ease of assembly and disassembly of said closure member.

9. The breast pump of claim 6 wherein substantially all components of said closure member are made of a transparent or translucent material to facilitate control of operation and maintenance of said pump.

10. A breast pump comprising a milk reservoir and a closure member for connection with said reservoir; said closure member comprising a suction bell and a suction pump suitable for single-handed operation and including: (a) a cylinder integrally connected with said closure member; and (b) a bellows located within said cylinder and provided with a flexible conduit for connection with an external source of oscillating subatmospheric pressure wherein the pump is operated mechanically by said external source.

* * * * *